(12) United States Patent
Sekar et al.

(10) Patent No.: US 10,688,072 B2
(45) Date of Patent: Jun. 23, 2020

(54) MISOPROSTOL DISPERSIBLE TABLET

(71) Applicant: Azanta Danmark A/S, Valby (DK)

(72) Inventors: Selvaraj Sekar, Tamilnadu (IN);
Elumalai Baskar, Tamilnadu (IN);
Arunachalam Malaiarasan, Tamilnadu (IN); Venugopal Prabhakaran, Tamilnadu (IN)

(73) Assignee: Azanta Danmark A/S, Valby (DK)

( * ) Notice: Subject to any disclaimer, the term of this patent is extended or adjusted under 35 U.S.C. 154(b) by 113 days.

(21) Appl. No.: 15/324,395

(22) PCT Filed: Jul. 10, 2015

(86) PCT No.: PCT/DK2015/050216
§ 371 (c)(1),
(2) Date: Jan. 6, 2017

(87) PCT Pub. No.: WO2016/004960
PCT Pub. Date: Jan. 14, 2016

(65) Prior Publication Data
US 2017/0173045 A1    Jun. 22, 2017

Related U.S. Application Data

(63) Continuation of application No. 14/329,023, filed on Jul. 11, 2014, now abandoned.

(30) Foreign Application Priority Data

Jul. 11, 2014   (EP) .................................... 14176821

(51) Int. Cl.
| | | |
|---|---|---|
| A61K 31/215 | (2006.01) | |
| A61K 9/00 | (2006.01) | |
| A61K 9/20 | (2006.01) | |
| A61K 31/5575 | (2006.01) | |

(52) U.S. Cl.
CPC ............ *A61K 31/215* (2013.01); *A61K 9/006* (2013.01); *A61K 9/0034* (2013.01); *A61K 9/0056* (2013.01); *A61K 9/2027* (2013.01); *A61K 9/2054* (2013.01); *A61K 9/2059* (2013.01); *A61K 31/5575* (2013.01); *A61K 2121/00* (2013.01)

(58) Field of Classification Search
CPC .............. A61K 31/215; A61K 31/5575; A61K 9/0034; A61K 9/006; A61K 9/2027; A61K 9/2059; A61K 9/0056; A61K 9/2054; A61K 2121/00
USPC ...................................................... 514/530
See application file for complete search history.

(56) References Cited

U.S. PATENT DOCUMENTS

| | | | |
|---|---|---|---|
| 3,917,864 A | 11/1975 | Karim | |
| 4,335,097 A | 6/1982 | David et al. | |
| 5,993,856 A | 11/1999 | Ragavan et al. | |
| 6,228,213 B1 | 5/2001 | Hanna et al. | |
| 6,664,290 B1 | 12/2003 | El-Rafaey | |
| 8,148,560 B2 | 4/2012 | Ahmed et al. | |
| 2005/0100600 A1 | 5/2005 | Staniforth | |
| 2005/0169986 A1 | 8/2005 | Tian et al. | |
| 2006/0115528 A1 | 6/2006 | Skulj | |
| 2008/0312168 A1 | 12/2008 | Pligaonkar et al. | |
| 2010/0260825 A1 | 10/2010 | Nair | |
| 2010/0297031 A1 | 11/2010 | Ubeda Perez et al. | |
| 2012/0077888 A1 | 3/2012 | Ramtoola et al. | |

FOREIGN PATENT DOCUMENTS

| | | | |
|---|---|---|---|
| CN | 1939308 A | 4/2007 | |
| CN | 102302443 A | 1/2012 | |
| CN | 102697746 | 10/2012 | |
| CN | 102872024 | 1/2013 | |
| CN | 102872024 A * | 1/2013 | ......... A61K 31/5575 |
| CN | 103040842 A | 4/2013 | |
| CN | 103340837 A | 10/2013 | |
| EP | 0574185 A2 | 6/1993 | |
| EP | 1987820 A1 | 11/2008 | |
| EP | 2689781 A1 | 1/2014 | |
| EP | 2689802 A1 | 1/2014 | |
| JP | H06199779 A | 7/1994 | |
| RU | 2394814 C1 | 7/2010 | |
| WO | 1996009825 A1 | 4/1996 | |
| WO | 2001013836 A1 | 3/2001 | |
| WO | 2002092097 A1 | 11/2002 | |
| WO | 2004000197 A2 | 12/2003 | |
| WO | 2006125450 A1 | 11/2006 | |
| WO | 2006133048 A2 | 12/2006 | |

(Continued)

OTHER PUBLICATIONS

Drugs.com (Cytotec—FDA prescribing information, side effects and uses, (Rev. Jul. 2017), [Retrieved from internet <URL: https://www.drugs.com/pro/cytotec.html >], 16 pages) (Year: 2017).*

Elhassan et al. (Sublingual compared with oral and vaginal misoprostol for labor induction, International Journal of Gynecology & Obstetrics (Jun. 2007) 97 (2): 153-154 (3 pages with cover)) (Year: 2007).*

Krause et al. (Off-label use of misoprostol for labor induction: a nation-wide survey in Switzerland, European Journal of Obstetrics & Gynecology and Reproductive Biology 159 (2011) 324-328) (Year: 2011).*

(Continued)

*Primary Examiner* — Mark V Stevens
(74) *Attorney, Agent, or Firm* — Verrill Dana, LLP

(57) ABSTRACT

The present invention relates to a solid pharmaceutical formulation comprising misoprostol or a pharmaceutically acceptable salt thereof. In particular, the invention relates to a dispersible tablet comprising misoprostol or a pharmaceutically acceptable salt thereof, providing alternative routes of administration. The tablet is particularly suited for cervical ripening, induction of labor, prevention and/or treatment of postpartum or post-abortion hemorrhage.

24 Claims, 4 Drawing Sheets

(56) References Cited

FOREIGN PATENT DOCUMENTS

| WO | 2007035954 A2 | 3/2007 |
| WO | 2009043844 A2 | 4/2009 |
| WO | 2009154810 A2 | 12/2009 |
| WO | 2010036878 A1 | 4/2010 |
| WO | 2010120345 A1 | 10/2010 |
| WO | 2011156812 A2 | 12/2011 |
| WO | 2014016390 A1 | 1/2014 |
| WO | 2014016394 A1 | 1/2014 |

OTHER PUBLICATIONS

Pfizer (Safety Data Sheet—Misoprostol tablets, (Rev. Oct. 27, 2014), [Retrieved from internet <URL: https://www.pfizer.com/system/files/products/material_safety_data/Misoprostol_Tablets_27-Oct-2014.pdf (Year: 2014).*

European Pharmacopoeia (8th Edition), chapter: Maize Starch, pp. 2684 (1 page) (2014).

European Pharmacopoeia (8th Edition), chapter: Potato Starch, pp. 3078 (1 page) (2014).

European Pharmacopoeia (8th Edition), 2014, chapters: 2.9.3. Dissolution Test for Solid Dosage Forms, pp. 288-295 (8 pages) (2012).

European Pharmacopoeia (8th Edition), chapter: Rice Starch, pp. 3163 (1 page) (2014).

European Pharmacopoeia (8th Edition), chapter: Wheat Starch, pp. 3563 (1 page) (2014).

European Pharmacopoeia (8th Edition), chapter: Pea Starch, pp. 3799 (1 page) (2014).

European Pharmacopoeia (8th Edition), chapter: Oromucosal Preparations, pp. 793-796 (4 pages) (2014).

European Pharmacopoeia (8th Edition), chapter: 2.9.1. Disintegration of Tablets and Capsules, pp. 285-287 (3 pages) (2011).

European Pharmacopoeia (8th Edition), chapter: 2.9.43 Apparent Dissolution, pp. 361-362 (2 pages) (2008).

Ashland, Inc., Polyplasdone crospovidone superdisintegrants—Product Overview, Ashland (2013) www.ashland.com/products/polyplasdone-crospovidone, 4 pages.

Piriyaprasarth et al. "Effect of source variation on drug release from HPMC tablets: Linear regression modeling for prediction of drug release," International Journal of Pharmaceutics, vol. 411, pp. 36-42 (2011).

Bagnasco et al. "Absorption and distribution kinetics of the major Parietaria judaica allergen (Par j 1) administered by noninjectable routes in healthy human beings," Journal of Allergy and Clinical Immunology, vol. 100, No. 1, pp. 122-129 (1997).

Torres-Lugo et al. "Molecular Design and in Vitro Studies of Novel pH-Sensitive Hydrogels for the Oral Delivery of Calcitonin," Macromolecules, vol. 32, pp. 6646-6651 (1999).

Salsa et al. "Oral Controlled-Release Dosage Forms. I. Cellulose Ether Polymers in Hydrophilic Matrices," Drug Development and Industrial Pharmacy, vol. 23, No. 9, pp. 929-938 (1997).

Frokjaer et al. "Protein Drug Stability: A Formulation Challenge," Nature Reviews, vol. 4, pp. 298-306 (2005).

Schmaljohann "Thermo- and pH-responsive polymers in drug delivery," Advanced Drug Delivery Reviews, vol. 58, pp. 1655-1670 (2006).

Wang et al. "Lubrication in tablet formulation," European Journal of Pharmaceutics and Biopharmaceutics, vol. 75, pp. 1-15 (2010).

Paisarntantiwong et al. "A comparison between single dose of 50 microg oral misoprostol and 25 microg vaginal misoprostol for labor induction", Journal of the Medical Association of Thailand, vol. 88, suppl. 2 pp. S56-S62 (2005), (8 pages including cover).

Krause et al. "Off-label use of misoprostol for labor induction: a nation-wide survey in Switzerland", European Journal of Obstetrics & Gynecology and Reproductive Biology, vol. 151, pp. 324-328 (2011).

Gopinath et al. "A Brief Review on Disintegrants", Journal of Chemical and Pharmaceutical sciences, vol. 5, Issue 3, pp. 105-112 (2012).

Tang et al. "Misoprostol: Pharmacokinetic profiles, effects on the uterus and side-effects", International Journal of Gynecology & Obstetrics, pp. 160-167 (2007).

Shihora et al., Superdisintegrants, Utility in Dosage Forms: A Quick Review, Journal of Pharmaceutical Science and Bioscientific Research (JPSBR), Nov.-Dec. 2011; 1 (3): 148-153.

United States Pharmacopeia (2008), <701> Disintegration, p. 1, Apparatus, [Retrieved from internet <URL: http://www.usp.org/sites/default/files/usp_pdf/EN/USPNF/generalChapter701.pdf >], 3 pages.

www.urmc.rochesteredu/encyclopedia/content.aspx?ContentTypeID=90&ContentID=P02021; Stomach and Duodenal Ulcers (Peptic Ulcers) in Children; retrieved on Dec. 18, 2015, 4 pages.

Tang et al., "Pilot study on the due of sublingual misoprostol with mifepristone in termination of first trimester pregnancy up to 9 weeks gestation", Human Reproduction, 2002, vol. 17, No. 7, pp. 1738-1740.

American Univ. (Clinical Trails.gov, Sublingual versus Vaginal Misoprostol for Labor Induction at Term, sponsored by American University of Beirut Medical Center (last updated Jul. 12, 2012), [Retrieved from internet <URL: https://clinicaltrials.govict2/show/NCT00140114?term=misoprostol+and+labor+and+sublingual&rank=3 >], 6 pages).

Watkinson et al., Misoprostol in peptic ulcer disease, Prostglandins (1987) 33 Suppl.: 78-92, [Retrieved from Internet <URL: http://www.ncbi.nlm.nih.gov/pubmed/3122278 >1; Abs. only (2 pages).

PDR (Misoprostol tablet, PDR3D, Apotheca Inc. (2010), 12 pages).

Merck (Misoprostol, Merck Index Online (2013), 1 page).

Medterms (Definition of Prostaglandin, MedicineNet (2014) [Retrieved from internet <URL: http://www.medterms.com/script/main/artasp?articlekey=16461&pf=2 >1) (1 page).

Tang et al. "Pharmacokinetics of different routes of administration of misoprostol," Human Reproduction, vol. 17, No. 2, pp. 332-336 (2002).

Habib et al. "Fast-Dissolve Drug Delivery Systems," Critical Reviews in Therapeutic Drug Carrier Systems, vol. 17, No. 1, pp. 61-72 (2000).

Rowe et al., Starch, Handbook of Pharmaceutical Excipients (7th Edition), pp. 784, Pharmaceutical Press (2012).

Mangal et al. "Superdisintegrants: An updated review," International Journal of Pharmacy and Pharmaceutical Science Research, vol. 2, No. 2, pp. 26-35 (2012).

Kumar et al. "Fundamental Aspects of Superdisintegrants: A Concise Review," Journal of Global Pharma Technology, vol. 4, No. 02, pp. 1-12 (2012).

Siddiqui et al. "A Short Review on "A Novel Approach in Oral Fast Dissolving Drug Delivery Systems and Their Patents"," Advances in Biological Research, vol. 5, No. 6, pp. 291-303 (2011).

Dressman et al. "Dissolution Testing as a Prognostic Tool for Oral Drug Absorption: Immediate Release Dosage Forms," Pharmaceutical Research, vol. 15, No. 1, pp. 11-22 (1998).

Divate et al. "Fast Disintegrating tablets—an emerging trend," International Journal of Pharmaceuticals Sciences Review and Research, vol. 6, No. 2, pp. 18-22 (2011).

Vivek et al. "Fast Dissolving Tablets: An Overview," International Journal of Pharmaceutical Sciences Review and Research, vol. 12, No. 1, pp. 35-41 (2012).

Desai et al. "Functionality of Disintegrants and Their Mixtures in Enabling Fast Disintegration of Tablets by a Quality by Design Approach," American Association of Pharmaceutical Scientists (APPS), vol. 15, No. 5, 12 pages (2014).

Panigrahi et al. "Effect of Combination of Superdisintegrants on Fast Dissolving Tablet of Gliclazide," WebmedCentral (Pharmaceutical Sciences), vol. 3, No. 4, pp. 1-16 (2012).

Amaral et al. "Effect of Hydroxypropyl Methylcellulose and Hydrogenated Castor Oil on Naproxen Release From Sustained-Release Tablets," AAPS PharmSciTech, vol. 2, No. 2, pp. 1-8 (2001).

Bennett et al. "A Masked Randomized Comparison of Oral and Vaginal Administration of Misoprostol for Labor Induction," Obstetics and Gynecology, vol. 92, No. 4, Part 1, pp. 481-486 (1998).

Shetty et al. "A comparison of oral and vaginal misoprostol tablets in induction of labour at term," British Journal of Obstetrics and Gynaecology, vol. 108, pp. 238-243 (2001).

(56) References Cited

OTHER PUBLICATIONS

Santos et al. "Tablet Compression," Pharmaceutical Manufacturing Handbook: Production and Processes, pp. 1133-1163, Chap. 6.6 (2008).
Mohanachandran et al. "Superdisintegrants: an overview," International Journal of Pharmaceutical Sciences Review and Research, vol. 6, No. 1, pp. 105-109 (2011).
Miller et al. "Pharmaceutical tablet lubrication," International Journal of Pharmaceutics, vol. 41, pp. 1-19 (1988).
Amin et al. "Superdisintegrants an economical alternative," Pharma Focus Asia, 3 pages, (2006) www.pharmafocusasia.com/manufacturing/superdisintegrants.htm.
Camarco et al. "Selecting Superdisintegrants for Orally Disintegrating Tablet Formulations," Pharmaceutical Technology, vol. 34, pp. 28-37 (2006) www.pharmtech.com/pharmtech/article/articleDetail.jsp?id=378398.
Bala et al. "Polymers in fast disintegrating tablets—a review," Asian Journal of Pharmaceutical and Clinical Research, vol. 5, No. 2, pp. 8-14 (2012).
Parveen et al. "Comparison of sublingual, vaginal, and oral misoprostol in cervical ripening for first trimester abortion," Indian Journal of Pharmacology, vol. 43, No. 2, pp. 172-175 (2011).
Astle et al. "Expression and regulation of prostaglandin E synthase isoforms in human myometrium with labour," Molecular Human Reproduction, vol. 13, No. 1, pp. 69-75 (2007).
Bauer "Misoprostol Preclinical Pharmacology," Digestive Diseases and Science, vol. 30, No. 11, pp. 118S-125S (1985).
U.S. Food and Drug Administration, "Misoprostol (marketed as Cytotec) Information," U.S. Department of Health & Human Services, 2pages, May 2009, www.fda.gov.
World Health Organization, WHO recommendations for induction of labour, 39 pages, (2011) www.who.int/iris/handle/10665/44531#sthash.6H0dFDkA.pdf.
Pharmacia, Cytotec 200 microgram Tablets (Misoprostol), Package leaflet: Information for the user, Feb. 2010, 2 pages.
Choksuchat "Clinical Use of Misoprostol in Nonpregnant Women: Review Article," The Journal of Minimally Invasive Gynecology, vol. 17, No. 4, pp. 449-455 (2010).
Hofmeyr et al. "Vaginal misoprostol for cervical ripening and induction of labour (Review)," The Cochrane Library, Issue 1, 315 pages, (2003).
Alfirevic et al. "Oral misoprostol for induction of labour (Review)," The Cochrane Library, Issue 2, 78 pages, (2006).
Gupta et al. "Comparative evaluation of 25 μg and 50 μg of intravaginal misoprostol for induction of labor," The Journal of Obstetrics and Gynecology of India, vol. 60, No. 1, pp. 51-54 (2010).
Kundodyiwa et al. "Low-dose oral misoprostol for induction of labor: a systematic review," Obstetrics & Gynecology, vol. 113, No. 2, Part 1, pp. 374-383 (2009).
Szczesny et al. "Pre-induction cervical ripening with 25 μg and 50 μg vaginal misoprostol in 181 nulliparous parturients," The Journal of Maternal-Fetal & Neonatal Medicine, vol. 22, No. 3, pp. 265-268 (2009).
Cecatti et al. "Effectiveness and safety of a new vaginal misoprostol product specifically labeled for cervical ripening and labor induction," Acta Obstetricia et Gynecologica, vol. 85, pp. 706-711 (2006).
Castaneda et al. "Misoprostol dose selection in a controlled-release vaginal insert for induction of labor in nulliparous women," American Journal of Obstetrics and Gynecology, vol. 193, pp. 1071-1075 (2005).
Elhassan et al. "Cervical ripening and labor induction with 25 μg vs. 50 μg of intravaginal misoprostol," International Journal of Gynecology & Obstetrics, vol. 90, pp. 234-235 (2005).
Has et al. "Comparison of 25 μg and 50 μg Vaginally Administered Misoprostol for Preinduction of Cervical Ripening and Labor Induction," Gynecologic and Obstetric Investigation, vol. 53, pp. 16-21 (2002).
Sanchez-Ramos et al. "Labor Induction With 25 μg Versus 50 μg Intravaginal Misoprostol: A Systematic Review," The American College of Obstetricians and Gynecologists, vol. 99, No. 1, pp. 145-151 (2002).
Ghidini et al. "Randomized controlled trial of 50 and 100 mcg of misoprostol for induction of labor at term," Archives of Gynecology and Obstetrics, vol. 265, pp. 128-130 (2001).
Feitosa et al. "Sublingual vs. vaginal misoprostol for induction of labor," International Journal of Gynecology & Obstetrics, vol. 94, pp. 91-95 (2006).
Meydanli et al. "Labor induction post-term with 25 micrograms vs. 50 micrograms of intravaginal misoprostol," International Journal of Gynecology & Obstetrics, vol. 81, pp. 249-255 (2003).
Villano et al. "A dose-finding study of oral misoprostol for labor augmentation," American Journal of Obstetrics and Gynecology, vol. 204 pp. 560.e1-560.e5 (2011).
Ding et al. "Low dose intravaginal misoprostol for induction of labor at term," International Journal of Gynecology and Obestetrics, vol. 90, pp. 72-73 (2005).
Komala et al. "Comparative Study of Oral and Vaginal Misoprostol for Induction of Labour, Maternal and Foetal Outcome," Journal of Clinical and Diagnostic Research, vol. 7, No. 12, pp. 2866-2869 (2013).
Loto et al. "Comparative study of the outcome of induction of labor using 25 μg and 50 μg of vaginal misoprostol," The Journal of Maternal-Fetal & Neonatal Medicine, vol. 25, No. 11, pp. 2359-2362 (2012).
Ewert et al. "Controlled-Release Misoprostol Vaginal Insert in Parous Women for Labor Induction: A Randomized Controlled Trial," Obstetrics & Gynecology, vol. 108, No. 5, pp. 1130-1137 (2006).
Danielsson et al. "Comparison Between Oral and Vaginal Administration of Misoprostol on Uterine Contractility," Obstetrics & Gynecology, vol. 93, No. 2, pp. 275-280 (1999).
Häusler et al. "Comparison of native starches as tablet disintegrants," Roquette Pharma, 2 pages (2009) www.roquette-pharma.com/white-paper/starch-excipient-tablet-disintegrant-pea-starch-filler-binder/.
Desai et al. "Understanding Disintegrant Action by Visualization," Journal of Pharmaceutical Sciences, vol. 101, No. 6, pp. 2155-2164 (2012).
Patra et al. "In Vitro Evaluation of Domperidone Mouth Dissolving Tablets," Indian Journal of Pharmaceutical Sciences, vol. 72, No. 6, pp. 822-825 (2010).
Surbek "Misoprostol for labor induction in term pregnancy", Eur Clinics Obstet Gynaccol (2007) 3:25-29.
Priyanka et al. "A Review Article on: Superdisintegrants", International Journal of Drug Research and Technology, 2013, vol. 3 (4), 76-87, ISSN 2277-1506.
Cheng et al. "Titrated oral compared with vaginal misoprostol for labor induction: a randomized controlled trial.", Obstet Gynecol. Jan. 2008;111(1):119-25.
Eikelder et al. "Induction of labour with a Foley catheter or oral misoprostol at term: the PROBAAT-II study, a multicentre randomised controlled trial.", BMC Pregnancy Childbirth. Mar. 19, 2013;13:67, 6 pages.
Wing et al. "A comparison of orally administered misoprostol with vaginally administered misoprostol for cervical ripening and labor induction", Am J Obstet Gynecol. May 1999;180(5):1155-60.
Alfirevic et al. "Oral misoprostol for induction of labour (Review)", The Cochrane Library 2014, Issue 6, 342 pages.
Disintegration Test for Suppositories and Vaginal Tablets, Appendix X B, Section II, Chinese Pharmacopoeia (2005), 4 pages.
Cytotec—FDA prescribing information, side effects and uses, 2017, [Retrieved from Internet <www.drugs.com/pro/cytotec.html > (16 pages).
Ac-Di-Sol—DuPont—Danisco, 2017, Retrieved from internet <www.danisco.com/pharmaceuticals/pharmaceutical-products/ac-di-sol/ > (2 pages).
Suryadevara V et al. "Studies on jackfruit seed starch as a novel natural superdisintegrant for the design and evaluation of irbesartan fast dissolving tablets.", Integr Med Res. Sep. 2017;6(3):280-291. doi: 10.1016/j.imr.2017.04.001. Epub May 26, 2017.

(56) References Cited

OTHER PUBLICATIONS

Elhassan, E.M., et al., "Misoprostol vs. oxytocin for induction of labor", International Journal of Gynecology and Obstetrics (2005) 91, 254-255.

Elhassan, M., et al., "Intravaginal misoprostol vs. dinoprostone as cervical ripening and labor-inducing agents", International Journal of Gynecology and Obstetrics 85 (2004) 285-286.

Aggarwal, N. et al., "Use of Misoprostol for Control of Post-Partum Haemorrhage in a Case of Aplastic Anaemia", Bull PGI, (2005), 39, pp. 121-122.

Asherkaci, H.M. et al., "Misoprostol usefulness on Post Partum Hemorrhage (PPH) among high risk mothers", Jamahiriya Medical Journal, (2010), 10, pp. 213-215.

Cabero Roura, L. et al., "Post-partum haemorrhage: Diagnosis, prevention and management", The Journal of Maternal-Fetal and Neonatal Medicine, May 2009, 22(S2), pp. 38-45.

Carbonell I Esteve, J.L., "Active management of the third phase of labour plus 400 μg of sublingual misoprostol and 200 μg of rectal misoprostol versus active management only in the prevention of post-partum haemorhage. A randomised clinical trial", Porg Obstet Gnecol, (2009); 52(10), pp. 543-551.

Casey, F. et al., "A randomized double-blinded comparison of same-day mifepristone and misoprostol with misoprostol only for cervical preparation in second-trimester surgical abortion", Abstracts/Contraception, (2014), 90, pp. 292-297.

Chaudhuri P., et al., "Rectally administrated misoprostol as an alternative to intravenous oxytocin infusion for preventing postpartum hemorrhage after cesarean delivery", J. Obstet. Gynaecol. Res., Sep. 2014, vol. 40, No. 9, pp. 2023-2030.

Hashima-E-Nasreen, "Oral misoprostol for preventing postpartum haemorrhage in home births in rural Bangladesh: how effective is it?", Global Health Action, (2011), 4:1, 7017, 11 pgs., DOI: 10.3402/gha.v4i0.7017.

Majeed, T. et al., "Comparison of Side Effects and Complications of Intravaginal Misoprostol with Extra-Amniotic Prostaglandin F2 Alpha for Termination of Second Trimester Pregnancy", Med. Forum, Dec. 2010, vol. 21, No. 12, 4 pgs.

Okonofua, F.E., "Assessment of sublingual misoprostol as first-line treatment for primary post-partum hemorrhage: Results of a multicenter trial", J. Obstet. Gynaecol, Res., Mar. 2014, vol. 40, No. 3, pp. 718-722.

Tewatia, R., et al., "Sublingual misoprostol versus intravenous oxytocin in prevention of post-partum hemorrhage", Arch. Gynecol. Obstet., Sep. 18, 2013, DOI 10.1007/s00404-013-3026-2.

Winikoff, B., et al., "Treatment of post-partum haemorrhage with sublingual misoprostol versus oxytocin in women not exposed to oxytocin during labour: a double-blind, randomised, non-inferiority trial", Lancet, (2010), vol. 375, pp. 210-216c.

Nagar, P. et al., "Orally disintegrating tablets: formulation, preparation techniques and evaluation", Journal of Applied Pharmaceutical Science 01 (04); 2011: 35-45.

Shetty, A. et al., "Sublingual misoprostol for the induction of labor at term", American Journal of Obstetrics and Gynecology, vol. 186, No. 1, Jan 2002, p. 72-76.

Zulfiker, Ah. et al., "Formulation development using maize starch & avicel PH101 as disintegrating agents and their effect on physical characteristics & in vitro release profile", International Journal of Pharmaceutical Sciences and Research, 2011; vol. 2(8): 2136-2141.

* cited by examiner

MISOPROSTOL DISPERSIBLE TABLET

The present invention relates to a solid pharmaceutical formulation comprising misoprostol or a pharmaceutically acceptable salt thereof. In particular, the invention relates to a dispersible tablet comprising misoprostol or a pharmaceutically acceptable salt thereof, providing alternative routes of administration. The tablet is particularly suited for use in obstetrics such as cervical ripening, induction of labor, prevention and/or treatment of postpartum or post-abortion hemorrhage depending on dosage and administration. Further, the present invention concerns a pharmaceutical composition, which is an immediate release tablet for use in obstetrics.

TECHNICAL BACKGROUND

Prostaglandins (PGs) have been associated with the onset of labor in women. Naturally occurring PGs are potent stimulants of human uterine contractility at any stage of pregnancy and also cause cervical ripening.

Induction of labor is defined as the process of artificially stimulating the uterus to start labor. It may be performed by administering oxytocin or prostaglandins to the pregnant woman. Labor induction is one of the most frequent procedures in pregnant women.

Cytotec and Misofar are commercially available misoprostol products, which comprise an extended release agent, hydrogenated castor oil.

The International patent application WO 2006/125450 A1 mentions the possibility of oral, sublingual, rectal or vaginal administration of misoprostol used in obstetric practice for controlling post-partum and post-abortive bleeding, and inducing labor or abortion. This application fails to disclose a pharmaceutical dosage form suitable for the mentioned administration forms.

The International patent application WO 2006/133048 A2 relates to a controlled release pharmaceutical gel for vaginal administration, the pharmaceutical gel comprising misoprostol, a cellulose derivative and a polyol, wherein the gel is a substantially nonaqueous gel which forms a hydrogel when placed in a vaginal tract.

The International patent application WO 2014/016394 A1 relates to the use of misoprostol for the induction of labor in a pregnant female, and in particular to the use of a sustained delivery device or insert containing 200 μg misoprostol for intravaginal use.

The International patent application WO 2007/035953 discloses vaginal tablets comprising misoprostol. The disclosed tablets comprise 100 μg misoprostol. A purported immediate release vaginal tablet and a sustained release vaginal tablet are disclosed, wherein the purported immediate release vaginal tablet are described as adhering to a tilted glass plate when placed on drops of water. Embodiments of the tablets are purported to adhere to an epithelial membrane. The vaginal tablets comprise lactose monohydrate, hydroxypropyl methylcellulose, corn starch and magnesium stearate. The vaginal tablets are manufactured by method steps comprising wet granulation, followed by drying in a fluid bed. The disclosed indications comprise cervical ripening and uterine contractions but not human labor.

SUMMARY OF THE INVENTION

Known misoprostol formulations for labor induction comprises at least one extended release agent and/or is intended for sustained delivery. In particular, existing misoprostol products for vaginal use comprise an extended release agent, such as hydrogenated castor oil, and/or are supposed to adhere to the vaginal tract of a subject.

Further, no misoprostol products for oral or sublingual use have yet been approved by regulatory agencies for induction of labor.

There is a need for a misoprostol product which is developed for both sublingual and oral administration, as guidelines on a national level as well as at the level of the individual hospital may suggest use of misoprostol through either route of administration.

These and other needs are met by aspects and embodiments of the present invention.

According to an aspect the present invention concerns a pharmaceutical composition comprising misoprostol or a pharmaceutically acceptable salt thereof, allowing an administration form selected among sublingual, oral and vaginal administration.

According to another aspect the present invention concerns a pharmaceutical composition comprising misoprostol or a pharmaceutically acceptable salt thereof, wherein said pharmaceutical composition allows at least sublingual administration, for the prevention or treatment of postpartum or post-abortion hemorrhage.

According to an aspect the present invention concerns a pharmaceutical composition comprising misoprostol or a pharmaceutically acceptable salt thereof, for use in obstetrics.

According to an aspect the invention concerns a method for obtaining cervical ripening or the induction of labor comprising administration of a pharmaceutical composition according to the invention. Preferably, the pharmaceutical formulation is used for female human subjects.

According to an aspect the present invention concerns a method for the prevention or treatment of postpartum or post-abortion hemorrhage, comprising administration of a pharmaceutical composition according to the invention.

According to an aspect the invention concerns a method for the manufacture of a pharmaceutical composition of the invention, wherein said pharmaceutical composition is a tablet and said method comprises a step of compression.

WHO recommends that all women giving birth should be offered uterotonics, preferably oxytocin, during the third stage of labour for the prevention of PHH (postpartum hemorrhage). Unfortunately oxytocin requires cool storage, sterile equipment and trained personnel, so that routine use of oxytocin in low-resource settings may be difficult. Misoprostol offers several advantages over oxytocin in that it may be formulated as a tablet; it is stable at ambient room temperature, widely available and less expensive. Further the administration of Misoprostol does not require any special skills, equipment, or facilities. In accordance with this, WHO recommends the use of alternatives to oxytocin such as Misoprostol in cases where oxytocin is not available, a skilled attendant is not present or if the patient does not respond to oxytocin. Thus, in places where geographic, financial, and infrastructure constraints often hinder the efforts of administering oxytocin, misoprostol could potentially have a significant impact on maternal morbidity and mortality.

Prompt recognition of excessive bleeding after delivery is crucial in the treatment of PHH. A healthy woman may lose 10-15% of her blood volume without a drop in blood pressure. By the time her blood pressure drops appreciably, the patient frequently has lost at least 30% of her blood volume. Thus, relying on vital signs to initiate treatment or to assess the severity of the bleeding could be misleading and may cause unnecessary delay in initiating appropriate treatment.

There is a need for a misoprostol product which may provide a consistent dose irrespective of the route of administration, such as vaginal, oral or sublingual.

Sublingual administration is associated with a rapid absorption and high peak levels compared to the oral administration route. This further result in an increased rate of onset of uterine contractions, as well as diminished variations in absorption making it easier to administer due to the more sustained effects compared to other administration routes.

However, the more rapid absorption and higher peak levels following sublingual administration may translate into increased gastrointestinal side effects. Thus, when the treatment with uterotonics are used in a preventive manner and therefore does not require a fast rate of onset, other routes of administration might prove advantageous. For example the oral, rectal or vaginal route of administration could to some extend reduce the degree of side effects. In correlation with this, WHO recommends that in the above mentioned cases where the use of oxytocin is not an option for preventing PPH, orally administered Misoprostol could be used as an alternative.

The vaginal or rectal route of administration seems advantageous especially in cases where the patient is vomiting or under anesthesia and therefore is unable to take oral medication.

According to the above mentioned reasons, there is an obvious need for a misoprostol product which is developed for both sublingual as well as other administration routes, such as oral, rectal or vaginal administration routes. This may provide advantages such as greatly enhance the ease of administration by persons not medically skilled, and/or allow for flexibility and continued adjustments during treatment with Misoprostol according to the individual case.

DETAILED DISCLOSURE

According to an embodiment, the present invention concerns a pharmaceutical composition comprising misoprostol or a pharmaceutically acceptable salt thereof, allowing an administration form selected among buccal, sublingual, oral and vaginal administration.

According to an embodiment, the present invention concerns a pharmaceutical composition comprising misoprostol or a pharmaceutically acceptable salt thereof, allowing an administration form selected among sublingual, oral and vaginal administration.

According to an embodiment, the present invention concerns the pharmaceutical composition, wherein said pharmaceutical composition allows sublingual administration.

Sublingual (abbreviated SL), from the Latin for "under the tongue", refers to the pharmacological route of administration by which drugs diffuse into the blood through tissues under the tongue.

When a chemical comes in contact with the mucous membrane beneath the tongue, it diffuses through it. Because the connective tissue beneath the epithelium contains a profusion of capillaries, the substance then diffuses into them and enters the venous circulation. In contrast, substances absorbed in the intestines are subject to "first-pass metabolism" in the liver before entering the general circulation.

Sublingual administration has certain advantages over oral administration. Being more direct, it is often faster, and it ensures that the substance will risk degradation only by salivary enzymes before entering the bloodstream, whereas orally administered drugs must survive passage through the hostile environment of the gastrointestinal tract, which risks degrading them, either by stomach acid or bile, or by the many enzymes therein, such as monoamine oxidase (MAO). Furthermore, after absorption from the gastrointestinal tract, such drugs must pass to the liver, where they may be extensively altered; this is known as the first pass effect of drug metabolism. Due to the digestive activity of the stomach and intestines and the solubility of the GI tract, the oral route is unsuitable for certain substances.

A phamacokinetic study in pregnant woman, who was to terminate their pregnancy before 12 weeks, investigated plasma levels after administration of 400 µg misoprostol (Tang O S, Schweer H, Seyberth H W, Lee S W, Ho P C; Pharmacokinetics of different routes of administration of misoprostol. Hum Reprod 2002 February; 17(2):332-6). Sublingual administration provided a larger peak in plasma concentration of misoprostol than oral and vaginal, and oral administration provided a larger peak than vaginal administration. The inter-subject variability in % at peak concentration was smaller following the sublingual route of administration than for oral and vaginal application, and the inter-subject variability in % at peak concentration for the oral route of administration was smaller than for vaginal application. Lower inter-subject variability allows administration of a more precise dosage, providing fewer side-effects and improved efficacy.

While this would point to using the sublingual administration route, no one has successfully produced a sublingual misoprostol product before the present invention. Sublingual administration would appear to offer faster effective administration of misoprostol. This is likely to provide better efficacy and fewer side effects, as adjusting the dosage becomes easier.

According to an embodiment, the present invention concerns the pharmaceutical composition, wherein said pharmaceutical composition allows any administration form selected among sublingual and oral administration.

According to an embodiment, the present invention concerns the pharmaceutical composition, suitable for cervical ripening or the induction of labor upon administration to a subject.

According to an embodiment, the present invention concerns the pharmaceutical composition, providing a mean terminal half-life ($t_{1/2}$) of less than 0.60; preferably less than 0.55; more preferred less than 0.50; preferably less than 0.45 hours.

According to an embodiment, the present invention concerns the pharmaceutical composition, providing a mean duration of induction to delivery of less than 25; preferably less than 24; more preferred less than 23; preferably less than 22; more preferred less than 21; preferably less than 20; more preferred less than 19; preferably less than 18 hours.

According to an embodiment, the present invention concerns a pharmaceutical composition comprising misoprostol or a pharmaceutically acceptable salt thereof, wherein said pharmaceutical composition allows at least sublingual administration, for the prevention or treatment of postpartum or post-abortion hemorrhage.

According to an embodiment, the present invention concerns the pharmaceutical composition, wherein said pharmaceutical composition further allows vaginal administration, preferably for the prevention or treatment of postpartum or post-abortion hemorrhage.

According to an embodiment, the present invention concerns a pharmaceutical composition comprising misoprostol or a pharmaceutically acceptable salt thereof, for use in obstetrics.

According to an embodiment, the present invention concerns the pharmaceutical composition, wherein said pharmaceutical composition allows any administration form selected among sublingual, oral and vaginal administration.

Misoprostol products of the prior art are designed to be placed in the vagina for a longer time period, inherently carrying the risk of falling out. Due to the requirement of the present composition of a very small amount of liquid, it appears to be suitable for a vaginal environment.

Providing a product which combines oral, sublingual and vaginal administration is complicated by the fact that oral administration have to take into account the varying pH conditions in the gastrointestinal tract, depending on location and timing of administration.

According to an embodiment, the present invention concerns the pharmaceutical composition, wherein misoprostol or a pharmaceutically acceptable salt thereof is the sole active ingredient. Naturally, according to this embodiment other inactive ingredients, i.e. excipients, may be present.

According to an embodiment, the present invention concerns the pharmaceutical composition, comprising a disintegrant comprising cross-linked PVP, preferably crospovidone. According to a preferred embodiment, the disintegrant is a superdisintegrant.

The cross-linked form of PVP is used as a disintegrant in pharmaceutical tablets.

Polyvinylpolypyrrolidone (polyvinyl polypyrrolidone, PVPP, crospovidone, crospolividone or E1202) is a highly cross-linked modification of polyvinylpyrrolidone (PVP), making it insoluble in water, though it still absorbs water and swells very rapidly generating a swelling force. This property makes it useful as a disintegrant in tablets.

Crospovidone may provide rapid disintegration in the mouth, and is particularly preferred for a pharmaceutical composition of the invention for buccal or sublingual administration.

Disintegrating agents are substances routinely included in the tablet formulations to aid in the break up of the compacted mass when it is put into a fluid environment. They promote moisture penetration and dispersion of the tablet matrix. In recent years, several newer disintegrants have been developed known as "Superdisintegrants". These newer substances are more effective at lower concentrations with greater disintegrating efficiency and mechanical strength. On contact with water the superdisintegrants swell, hydrate, change volume or form and produce a disruptive change in the tablet. Effective superdisintegrants provide improved compressibility, compatibility and have little negative impact on the mechanical strength of formulations. Commonly available superdisintegrants along with their commercial trade names are briefly described herewith.

Modified starches: Sodium starch glycolate which is the sodium salt of a carboxymethyl ether of starch. It is usually effective at a concentration of 2-8%. It can take up more than 20 times its weight in water and the resulting high swelling capacity combined with rapid uptake of water accounts for its high disintegration rate and efficiency. It is available in various grades i.e. Type A, B and C, which differ in pH, viscosity and sodium content.

Modified celluloses, Carboxymethylcellulose and its derivative (Croscarmellose Sodium): Cross-linked sodium carboxymethylcellulose is a white, free flowing powder with high absorption capacity. It has a high swelling capacity and thus provides rapid disintegration and drug dissolution at lower levels. It also has an outstanding water wicking capability and its cross-linked chemical structure creates an insoluble hydrophilic, highly absorbent material resulting in excellent swelling properties. Its usual recommended concentration is 0.5-2.0%, which can be used up to 5.0% L-HPC (Low substituted Hydroxy propyl cellulose). It is insoluble in water, swells rapidly and is usually used in the range of 1-5%. The grades LH-11 and LH-21 exhibit the greatest degree of swelling.

Cross-linked polyvinylpyrrolidone is a completely water insoluble polymer. It rapidly disperses and swells in water but does not gel even after prolonged exposure. The rate of swelling is highest among all the superdisintegrants and is usually effective at 1-3%. It acts by wicking, swelling and possibly some deformation recovery. The polymer has a small particle size distribution that imparts a smooth mouth feel to dissolve quickly.

Soy polysaccharide is a natural super disintegrant that does not contain any starch or sugar so can be used in nutritional products. Cross-linked alginic acid is insoluble in water and disintegrates by swelling or wicking action. It is a hydrophilic colloidal substance, which has high sorption capacity. It is also available as salts of sodium and potassium. Gellan gum is an anionic polysaccharide of linear tetrasaccharides, derived from *Pseudomonas elodea* having good superdisintegrant property similar to the modified starch and celluloses. Xanthan Gum derived from *Xanthomonas campestris* is official in the USP with high hydrophilicity and low gelling tendency. It has low water solubility and extensive swelling properties for faster disintegration. Calcium Silicate It is a highly porous, lightweight superdisintegrant, which acts by wicking action. Ion exchange resins The INDION 414 has been used as a superdisintegrant.

Superdisintegrants, such as natural or synthetic superdisintegrants, may be used for the present pharmaceutical compositions. Natural superdisintegrants used in formulations, comprise, but are not limited to the group consisting of: *Cassia fistula* gum, LepidumSativum, Locust Bean gum, *Plantago* ovate Mucilage, Seed powder, *Plantago ovata* Husk powder, and Treated Agar. Synthetic Superdisintegrants used in formulations, comprise, but are not limited to the group consisting of: crospovidone, Sodium Starch glycolate, Croscarmellose sodium (Ac-Di-Sol), kollidon CL, B-cyclodextrin, and Citric Acid and Sodium bicarbonate.

According to an embodiment, the present invention concerns the pharmaceutical composition, comprising at least two disintegrants.

According to an embodiment, the present invention concerns the pharmaceutical composition, wherein at least one of said at least two disintegrants is a cross-linked carboxymethylcellulose, preferably croscarmellose sodium.

A suitable disintegrant is a modified cellulose, preferably a modified carboxymethylcellulose, more preferred a cross-linked polymer of carboxymethylcellulose, preferably croscarmellose.

Croscarmellose sodium is an internally cross-linked sodium carboxymethylcellulose for use as a superdisintegrant in pharmaceutical formulations. The cross-linking reduces water solubility while still allowing the material to swell (like a sponge) and absorb many times its weight in water. As a result, it provides superior drug dissolution and disintegration characteristics, thus improving formulas subsequent bioavailability by bringing the active ingredients into better contact with bodily fluids.

According to an embodiment, the present invention concerns the pharmaceutical composition, wherein said at least two disintegrants use different mechanisms of disintegration. The expression "different mechanisms" also covers the case of partly overlap between the different mechanisms.

Disintegrants may be classified by mechanism of disintegration as noted below.

| Disintegrants classified by mechanism of disintegration | | |
|---|---|---|
| Mechanism of disintegration | Method | Examples of disintegrants |
| I. Swelling | The particles of the disintegrant swells when hydrated. The swelling pressure destroys the interaction between the other particles. | Croscarmellose sodium Starch Polyplasdone XL 10 |
| II. Porosity and Capillary Action (Wicking) | Facilitate the movement of fluid into the tablet. | Croscarmellose sodium Polyplasdone XL 10 |
| III. Disintegrating particle/Particle repulsive forces | Electric repulsive forces between particles arise when hydrated. | |
| IV. Deformation | The compression of tablets deform the particles, when in contact with water the particles return to their original size. | Starch Polyplasdone XL 10 |
| V. Chemical reaction (Acid-Base reaction) | Inside the tablet acid and base react and $CO_2$ is released creating a pressure that breaks the tablet apart. Highly sensitive to humidity and temperature. | |
| VI. Enzymatic Reaction | Enzymes present in the body breaks down the binder of the tablet. | |

According to an embodiment, the present invention concerns the pharmaceutical composition, wherein said at least two disintegrants use mechanisms of disintegration comprising swelling, porosity and capillary action, and deformation. In other words preferably all of the mechanisms, I. (swelling), II. (wicking) and IV. (deformation) are covered by said at least two disintegrants.

According to an embodiment, the present invention concerns the pharmaceutical composition, wherein said at least two disintegrants are superdisintegrants.

According to an embodiment, the present invention concerns the pharmaceutical composition comprising a disintegrant which is starch, preferably maize starch.

According to an embodiment, the present invention concerns the pharmaceutical composition, further comprising at least one superdisintegrant.

According to an embodiment, the present invention concerns the pharmaceutical composition, wherein said pharmaceutical composition comprises an excipient selected among the group consisting of Maize starch (also known as Corn starch), Potato starch, Pea starch, Rice starch, Tapioca starch (also known as Cassava or Manioc starch), Wheat starch, and Modified starch.

Formerly, Potato starch was commonly used as a disintegrant. Recently, the use of so-called superdisintegrants such as crospovidone, croscarmellose sodium, and sodium starch glycolate have become more popular.

Maize starch suffers from the drawback that tablets comprising maize starch tend to be hygroscopic and thus unstable. It has surprisingly been discovered that starch, in particular maize starch, is particularly preferred for solving the problems of the present invention. This is in particular true, if starch is combined with another disintegrant, preferably at least one superdisintegrant, more preferred at least two superdisintegrants.

According to an embodiment, the present invention concerns the pharmaceutical composition, wherein said pharmaceutical composition comprises maize starch.

According to an embodiment, the present invention concerns the pharmaceutical composition, wherein said pharmaceutical composition comprises an amount of disintegrant of 1-50%, preferably 2-30%, more preferred 3-25%, preferably 5-20%, more preferred 6-15%, preferably 8-12%, more preferred about 10%.

According to an embodiment, the present invention concerns the pharmaceutical composition, wherein said pharmaceutical composition comprises an amount of superdisintegrant of 1-50%, preferably 2-30%, more preferred 3-25%, preferably 5-20%, more preferred 6-15%, preferably 8-12%, more preferred about 10%.

According to an embodiment, the present invention concerns the pharmaceutical composition, wherein said pharmaceutical composition comprises an amount of croscarmellose sodium of 1-50%, preferably 2-30%, more preferred 3-25%, preferably 5-20%, more preferred 6-15%, preferably 8-12%, more preferred about 10%.

According to an embodiment, the present invention concerns the pharmaceutical composition, wherein said pharmaceutical composition comprises an amount of crospovidone of 1-50%, preferably 2-30%, more preferred 3-25%, preferably 5-20%, more preferred 6-15%, preferably 8-12%, more preferred about 10%.

According to an embodiment, the present invention concerns the pharmaceutical composition, wherein said pharmaceutical composition comprises an amount of starch of 1-50%, preferably 2-30%, more preferred 3-25%, preferably 5-20%, more preferred 6-15%, preferably 8-12%, more preferred about 10%.

According to an embodiment, the present invention concerns the pharmaceutical composition, wherein said pharmaceutical composition comprises an amount of maize starch of 1-50%, preferably 2-30%, more preferred 3-25%, preferably 5-20%, more preferred 6-15%, preferably 8-12%, more preferred about 10%.

According to an embodiment, the present invention concerns the pharmaceutical composition, wherein said pharmaceutical composition comprises an amount of microcrystalline cellulose of 1-99%, preferably 5-98%, more preferred 10-97%, preferably 20-95%, more preferred 30-90%, preferably 40-85%, more preferred 50-80%, preferably 60-75%, more preferred about 70%.

According to an embodiment, the present invention concerns the pharmaceutical composition, wherein said pharmaceutical composition comprises an amount of flow agent of 0.1-10%, preferably 0.2-5%, more preferred 0.3-4%, preferably 0.5-3%, more preferred 0.8-2%, preferably about 1%.

According to an embodiment, the present invention concerns the pharmaceutical composition, wherein said flow agent is colloidal silicon dioxide.

According to an embodiment, the present invention concerns the pharmaceutical composition, having a content of misoprostol or a pharmaceutically acceptable salt thereof, selected among 0.5-1000, 1-500, 2.5-250, 5-100, 10-50, 20-30, and 25 μg. In the case of a pharmaceutically acceptable salt the amount is preferably equivalent to an amount of misoprostol selected among 0.5-1000, 1-500, 2.5-250, 5-100, 10-50, 20-30, and about 25 μg.

According to an embodiment, the present invention concerns the pharmaceutical composition, having a content of misoprostol or a pharmaceutically acceptable salt thereof, selected among 0.001-2.0 mg; 0.002-1.5 mg; 0.0025-1.2 mg; 0.005-1.0 mg; 0.007-0.9 mg; 0.01-0.8 mg; 0.020-0.7 mg; 0.025-0.6 mg; 0.05-0.5 mg; 0.075-0.4 mg; 0.09-0.3 mg; and 0.1-0.2 mg.

According to an embodiment, the present invention concerns the pharmaceutical composition, having a content of misoprostol or a pharmaceutically acceptable salt thereof, of 0.2 mg or more than 0.2 mg.

According to an embodiment, the present invention concerns the pharmaceutical composition, having a content of misoprostol or a pharmaceutically acceptable salt thereof, selected among 0.005%-2%; 0.01%-1%; 0.02%-0.5%; and 0.024%-0.25% by weight of the pharmaceutical composition.

According to an embodiment, the present invention concerns the pharmaceutical composition, having a content of misoprostol or a pharmaceutically acceptable salt thereof, selected among less than 2%; less than 1%; less than 0.7%; less than 0.5%; less than 0.3% and less than 0.2% by weight of the pharmaceutical composition.

According to an embodiment, the present invention concerns the pharmaceutical composition, which is a tablet having a score-line. A score-line may also be known as a groove.

According to an embodiment, the present invention concerns the pharmaceutical composition, wherein said score-line allows fractional dosing. Preferably said score-line allows fractional dosing providing a consistent dosage of active ingredient.

According to an embodiment, the present invention concerns the pharmaceutical composition, wherein said score-line allows fractional dosing of ¼ or ¼ of the total dosage of said pharmaceutical composition. A tablet allowing fractional dosing provides dose flexibility. Preferably the tablets are suitable for administering the half dose or the quarter dose by splitting.

According to an embodiment, the present invention concerns the pharmaceutical composition having a disintegration time of no more than 15 minutes, preferably less than 15 minutes, more preferred less than 10 minutes, preferably less than 5 minutes, more preferred less than 3 minutes, preferably less than 2 minutes, more preferred less than 1 minute, preferably less than 45 seconds, more preferred less than 30 seconds, preferably less than 25 seconds, more preferred less than 20 seconds, preferably less than 19 seconds, more preferred less than 18 seconds, preferably less than 17 seconds, more preferred less than 16 seconds, preferably less than 15 seconds, more preferred less than 10 seconds, preferably less than 9 seconds, more preferred less than 8 seconds, preferably less than 7 seconds, more preferred less than 6 seconds.

The disintegration time is preferably measured using Disintegration apparatus A according to European Pharmacopoeia 8.0, placing one tablet in each of the 6 tubes of the basket without disc. The apparatus is operated using water medium as the immersion fluid, maintained at 37±2° C.

Short disintegration time does not only allow sublingual administration, but surprisingly appears to allow vaginal administration without the need of an extended release agent and/or adherence to the vaginal tract. A few drops of water, such as about ten drops or less, are sufficient to disintegrate compositions of the present invention. Thus, both sublingual and vaginal administration may be feasible.

Fast dissolving drug delivery provides a number of advantages, comprising improved patient compliance, ease of swallowing, no water needed, and accuracy of dosage (Walid Habib, Raj Khankari, and John Hontz, "Fast-Dissolve Drug Delivery Systems", Critical Reviews in Therapeutic Drug Carrier Systems, 17(1):61-72(2000)).

According to an embodiment, the present invention concerns the pharmaceutical composition, wherein said disintegration time is measured initially after manufacture, preferably 3 months after manufacture, more preferred 6 months after manufacture, preferably 9 months after manufacture, more preferred 12 months after manufacture, preferably 18 months after manufacture, more preferred 24 months after manufacture.

According to an embodiment, the present invention concerns the pharmaceutical composition, which allows dispersion of one or more of said pharmaceutical compositions in 100 ml water at 25° C. within 15 minutes, preferably within 10 minutes, more preferred within 5 minutes, preferably within 3 minutes, more preferred within 2 minutes, preferably within 1 minute, upon stirring, thereby providing a dispersion; said dispersion passing through a sieve screen with a nominal mesh aperture of 710 μm. Preferably the dispersion passes through the sieve screen without leaving any residue, e.g. as determined by visual inspection.

According to an embodiment, dispersion tests are performed with six (6) samples, and the average of the measured dispersion times is used.

According to an embodiment, the present invention concerns the pharmaceutical composition, which allows dispersion of one or more of said pharmaceutical compositions in 100 ml water at 25° C. within 1 minute, preferably less than 45 seconds, more preferred less than 30 seconds, preferably less than 25 seconds, more preferred less than 20 seconds, preferably less than 19 seconds, more preferred less than 18 seconds, preferably less than 17 seconds, more preferred less than 16 seconds, preferably less than 15 seconds, more preferred less than 10 seconds, preferably less than 9 seconds, more preferred less than 8 seconds, preferably less than 7 seconds, more preferred less than 6 seconds, upon stirring, thereby providing a dispersion; said dispersion passing through a sieve screen with a nominal mesh aperture of 710 μm.

According to an embodiment, the present invention concerns the pharmaceutical composition, which allows dispersion of one or more of said pharmaceutical compositions in 100 ml water at 25° C. within 15 minutes, preferably within 10 minutes, more preferred within 5 minutes, preferably within 3 minutes, more preferred within 2 minutes, preferably within 1 minute, substantially without stirring, thereby providing a dispersion; said dispersion passing through a sieve screen with a nominal mesh aperture of 710 μm. The expression "substantially without stirring" means that the pharmaceutical composition provides a dispersion spontaneously upon contact with water without the need of stirring, shaking or other form of agitation, or stirring up to a speed of 1 RPM.

According to an embodiment, the invention concerns a pharmaceutical composition or a tablet, which allows complete dispersion of one or more pharmaceutical compositions or tablets comprising a total of at least 100 μg misoprostol or a pharmaceutically acceptable salt thereof in 100 ml water at 25° C. upon stirring, thereby providing a dispersion; said dispersion passing through a sieve screen with a nominal mesh aperture of 710 μm. According to embodiments, the term "complete dispersion" covers the case wherein at least 90%, more preferred at least 95%, preferably at least 98%, more preferred 99%, preferably 100% misoprostol or a pharmaceutically acceptable salt thereof is dispersed or dissolved.

According to an embodiment, the present invention concerns the pharmaceutical composition, wherein said pharmaceutical composition is a tablet.

According to an embodiment, the invention concerns a pharmaceutical composition which is a dispersible tablet. The expression "dispersible tablet" refers to a tablet, which may be dispersed in water before administration, providing a homogeneous dispersion. Dispersible tablets disintegrate within 3 minutes using water at 15-25° C. The fineness of dispersion should comply with a test comprising placing 2 tablets in 100 ml water and stirring until completely dispersed. A smooth dispersion is produced, which passes through a sieve screen with a nominal mesh aperture of 710 μm.

According to an embodiment, the present invention concerns the pharmaceutical composition, which is a dispersible tablet, which may be dispersed in water before administration, providing a homogeneous dispersion; wherein said dispersible tablet disintegrates within 3 minutes using water at 15-25° C. forming a dispersion; wherein the fineness of said dispersion complies with a test comprising placing 2 tablets in 100 ml water and stirring until completely dispersed, whereby a preferably smooth dispersion is produced, which passes through a sieve screen with a nominal mesh aperture of 710 μm.

According to an embodiment, the present invention concerns the pharmaceutical composition, which is a dispersible tablet, which may be dispersed in water before administration, providing a homogeneous dispersion; wherein said dispersible tablet disintegrates within 3 minutes using water at 20° C. forming a dispersion; wherein the fineness of said dispersion complies with a test comprising placing 2 tablets in 100 ml water and stirring until completely dispersed, whereby a preferably smooth dispersion is produced, which passes through a sieve screen with a nominal mesh aperture of 900 μm, preferably 600 μm, more preferred 400 μm.

According to an embodiment, the present invention concerns the pharmaceutical composition, which is an orodispersible tablet.

An orodispersible or orally disintegrating tablet (ODT) is designed to be dissolved on the tongue rather than swallowed whole. The ODT may be used for patients who experience dysphagia (difficulty in swallowing). An additional reason to use an ODT is the convenience of a tablet that can be taken without water.

According to an embodiment, the present invention concerns the pharmaceutical composition, which is an immediate release tablet.

The term "immediate release" pharmaceutical formulation includes any formulation in which the rate of release of drug from the formulation and/or the absorption of drug, is neither appreciably, nor intentionally, retarded by galenic manipulations. Thus, the term excludes formulations which are adapted to provide for "modified", "controlled", "sustained", "prolonged", "extended" or "delayed" release of drug. In this context, the term "release" includes the provision (or presentation) of drug from the formulation to the gastrointestinal tract, to body tissues and/or into systemic circulation.

According to a preferred embodiment, the present invention concerns a pharmaceutical composition, which is an immediate release tablet for use in obstetrics.

According to an embodiment, the present invention concerns the pharmaceutical composition, which is free of any extended release agents. Examples of extended release agents comprise hydrogenated castor oil and hydrogenated vegetable oil.

According to an embodiment, the present invention concerns the pharmaceutical composition, further comprising a coating. While a preferred embodiment is a tablet without coating, another alternative is a tablet having a coating, e.g. to improve storage stability. Preferably said coating does not interfere with or substantially affect dispersibility.

According to an embodiment, the present invention concerns the pharmaceutical composition, further comprising at least one excipient, preferably selected among diluents, disintegrants, binders, glidants, lubricants, and coatings.

An excipient is generally a pharmacologically inactive substance. Examples include, but are not limited to, diluents, disintegrants, binders, glidants, lubricants, and coatings. Other examples of suitable excipients may be found in Handbook of Pharmaceutical Excipients, $7^{th}$ Ed. by Rowe, Raymond C. et al., Pharmaceutical Press, London.

Diluents are inactive ingredients that are added to tablets and capsules in addition to the active drug. Some very common diluents in tablets include starch, cellulose derivatives, and magnesium stearate (also a lubricant). Diluents fill out the size of a tablet or capsule, making it practical to produce and convenient for the consumer to use. By increasing the bulk volume, diluents make it possible for the final product to have the proper volume for patient handling. A good diluent must be inert, compatible with the other components of the formulation, non-hygroscopic, relatively cheap, compactable, and preferably tasteless or pleasant tasting. Plant cellulose (pure plant diluent) is a popular diluent in tablets or hard gelatin capsules. Dibasic calcium phosphate is another popular tablet diluent. A range of vegetable fats and oils can be used in soft gelatin capsules. Other examples of diluents include: lactose, sucrose, glucose, mannitol, sorbitol, calcium carbonate, and magnesium stearate.

Disintegrants may expand and dissolve when wet causing the tablet to break apart. They ensure that when the tablet is in contact with water, it rapidly breaks down into smaller fragments, facilitating dissolution or dispersion. Examples of disintegrants include, but are not limited to: crosslinked polymers, such as crosslinked polyvinylpyrrolidone (crospovidone), and crosslinked sodium carboxymethyl cellulose (croscarmellose sodium); and the modified starch sodium starch glycolate. Specific examples further include Indion 414, L-HPC, and pregelatinised starch.

Binders hold the ingredients in a tablet together. Binders ensure that tablets and granules can be formed with required mechanical strength, and give volume to tablets. Examples of binders include: saccharides and their derivatives: disaccharides, sucrose, lactose; polysaccharides and their derivatives, such as starches, cellulose or modified cellulose, such as microcrystalline cellulose and cellulose ethers such as hydroxypropyl cellulose (HPC); sugar alcohols such as xylitol, sorbitol or maltitol; further Protein: gelatin; and Synthetic polymers: polyvinylpyrrolidone (PVP), polyethylene glycol (PEG). Examples include gelatin, cellulose, cellulose derivatives, polyvinylpyrrolidone, starch, sucrose and polyethylene glycol. Other examples include cellulose, methyl cellulose, polyvinylpyrrolidone and polyethylene glycol.

Glidants are used to promote powder flow by reducing interparticle friction and cohesion. These are used in combination with lubricants as they have no ability to reduce die wall friction. Examples include fumed silica, talc, and magnesium carbonate.

Lubricants are agents added to tablet and capsule formulations to improve certain processing characteristics. Lubricants inter alia prevent ingredients from clumping together and from sticking to the tablet punches or capsule filling machine (see also: Miller T A et al., Pharmaceutical tablet lubrication, Int J Pharm 1988; 41: 1-19). Lubricants also ensure that tablet formation and ejection can occur with low friction between the solid and die wall. Common minerals like talc or silica, and fats, e.g. vegetable stearin, magnesium stearate or stearic acid are examples of lubricants used in tablets or hard gelatin capsules (see also: Wang J et al., Lubrication in tablet formulation, Eur J Pharm Biopharm 2010 May; 75(1): 1-15).

Coatings protect ingredients from deterioration by moisture in the air and make large or unpleasant-tasting tablets easier to swallow. For most coated tablets, a cellulose ether hydroxypropyl methylcellulose (HPMC) film coating is used which is free of sugar and potential allergens. Occasionally, other coating materials are used, for example synthetic polymers, shellac, corn protein zein or other polysaccharides. A specific example is Opadry. Capsules are coated with gelatin.

According to an embodiment, the present invention concerns a method for obtaining cervical ripening or the induction of labor comprising administration of a pharmaceutical composition according to the invention. Preferably the pharmaceutical formulation is used for female human subjects.

According to an embodiment, the present invention concerns the method, wherein 25-50 μg misoprostol, or an equivalent amount of a pharmaceutically acceptable salt thereof, is administered orally or sublingually every 2-4 hours or vaginally every 6 hours.

According to an embodiment, the present invention concerns the method, wherein 25-50 μg misoprostol, or an equivalent amount of a pharmaceutically acceptable salt thereof, is administered orally or sublingually every 2-4 hours.

According to an embodiment, the present invention concerns a method for the prevention or treatment of postpartum or post-abortion hemorrhage, comprising administration of a pharmaceutical composition according to the invention.

According to an embodiment, the present invention concerns the method, wherein an amount selected among 0.1-2.0 mg; 0.15-1.5 mg; 0.2-1.0 mg; 0.4-0.8 mg; and 0.5-0.6 mg misoprostol, or an equivalent amount of a pharmaceutically acceptable salt thereof, is administered vaginally, orally or sublingually.

According to an embodiment, the present invention concerns a method for the manufacture of a pharmaceutical composition, wherein said pharmaceutical composition is a tablet and said method comprises a step of compression.

According to an embodiment, the present invention concerns the method, wherein said tablet is manufactured by a method comprising a step of dry mixing followed by a step of direct compression.

According to an embodiment, the present invention concerns the method, wherein said tablet is manufactured by a method comprising a step of geometrical mixing of misoprostol or a pharmaceutically acceptable salt thereof, with at least one excipient. The term "excipient" indicates an ingredient, which is not an active pharmaceutical ingredient.

All cited references are incorporated by reference.

The accompanying Figures and Examples are provided to explain rather than limit the present invention. It will be clear to the person skilled in the art that aspects, embodiments and claims of the present invention may be combined.

Unless otherwise mentioned, all percentages are in weight/weight. Unless otherwise mentioned, all measurements are conducted under standard conditions (ambient temperature and pressure).

EXAMPLES

Example 1: A Composition of the Invention

The following ingredients were used to manufacture tablets:

| Ingredient | mg/Tablet | Ascribed function |
|---|---|---|
| Misoprostol (as 1% HPMC dispersion) | 2.50 | API |
| Microcrystalline Cellulose (PH 112) | 69.5 | Binder/Diluent/disintegrant |
| Starch Plain (maize starch) | 10.0 | Diluent/disintegrant |
| Croscarmellose Sodium (Ac-di-sol) | 10.0 | Super disintegrant |
| Polyplasdone XL10 (Crospovidone) | 10.0 | Super disintegrant |
| Colloidal Silicon Dioxide | 1.00 | Improves flow properties |
| | 103.0 | |

Misoprostol (as 1% HPMC dispersion) provides 2.50 mg/100 = 25 μg misoprostol per tablet.

FIG. 1 provides a flow chart of the manufacturing process.

Key steps of the applied process, which follows the procedure of FIG. 1, are described as follows:

Sifting:

Misoprostol and other excipients pass through 30# sieve.

Geometrical Mixing:

Step 1: Manually mix 75 g of Misoprostol (As 1% HPMC dispersion) with 75 g of Microcrystalline cellulose PH 112.

Step 2: Mix 150 g of step 1 blend with 150 g of Microcrystalline cellulose PH 112.

Step 3: Mix 300 g of step 2 blend with 300 g of Microcrystalline cellulose PH 112.

Step 4: Mix 600 g of step 3 blend with 600 g of Microcrystalline cellulose PH 112.

Load step 4 blend into the main bowl of planetary mixer and mix for 15 min.

Dry Mixing:

Then add remaining quantity of previously mixed Microcrystalline cellulose PH 112, Starch Plain, Cros carmellose sodium, Polyplasdone XL10 and Colloidal silicon dioxide and mix for 20 min.

Compression

Compress in a compression machine (using 7.5×4.5 mm-punch) (see also: Wang J et al., Lubrication in tablet formulation, Eur J Pharm Biopharm 2010 May; 75(1): 1-15 and Santos H M M et al.; Tablet Compression, Pharmaceutical Manufacturing Handbook 2008; 6.6: 1133-63).

Packing

A container closure system was selected. Based on pre-formulation studies and a stability study, misoprostol (1% HPMC Dispersion) is hygroscopic in nature and also susceptible to degradation in presence of heat, light and humidity. Thus the tablet requires additional packaging precautions to protect the drug substance from heat, high humidity and light. Based on a sample Alu/Alu packing is suitable for this product.

Example 2: Disintegration Time

The disintegration time of tablets manufactured according to Example 1 were measured initially (right after manufacture) as well as after several months. The tablets were packed in Alu-Alu blister packs, maintained at 30±2° C. and 65±5% RH. The disintegration time was measured according to European Pharmacopoeia 8.0, using Disintegration apparatus A, placing one tablet in each of the 6 tubes of the basket without disc. The apparatus was operated using water medium as the immersion fluid, maintained at 37±0.5° C. After disintegration of the tablets the basket was lifted from the fluid, and all of the tablets had disintegrated completely.

The measured disintegration times are provided in the table below.

| | Initial | 3$^{rd}$ month | 6$^{th}$ month | 9$^{th}$ month | 12$^{th}$ month | 18$^{th}$ month |
|---|---|---|---|---|---|---|
| Disintegration time | 4 seconds | 5 seconds | 5 seconds | 5 seconds | 6 seconds | 5 seconds |

The tablets were found to have satisfactory disintegration time and stability.

Example 3: Comparison Experiment I

In order to compare a tablet of the present invention with a tablet of the prior art, a tablet manufactured according to Example 1 ("Tablet A") was subjected to the test of Example 4 of WO 2007/035954. Tablet A was compared to a commercially available Cytotec misoprostol tablet.

Three drops of water were placed on a glass plate. A tablet was placed on the drops of water. The plate was then tilted at a 90 degree angle. Tablet A of the present invention immediately began to swell and disintegrate upon contacting the water. When the plate was tilted, the disintegrated Tablet A slid without adhering to the glass plate. The Cytotec tablet showed far greater adherence to the glass plate.

Due to the short disintegration time, Tablet A will immediately form a dispersion upon contact with water or an aqueous medium. Therefore, Tablet A is not dependent on adherence to the vaginal tract upon administration.

Example 4: Comparison Experiment I—Disintegration

A tablet of the present invention was compared with a tablet of the prior art. A tablet manufactured according to Example 1 ("Tablet A") was compared to a commercially available Cytotec misoprostol 0.2 mg tablet. Each tablet was placed in a beaker with a few drops of water. Photographs were recorded after 3, 7 and 15 seconds. Between each photograph, the beakers were very gently agitated by rotating the beakers.

A dispersion is formed immediately after bringing Tablet A in contact with water. For Cytotec, no dispersion is formed, large flakes are formed, and the Cytotec tablet is not suitable for sublingual administration. Further, vaginal administration would require the Cytotec tablet to stay for a prolonged time in the vaginal tract.

Example 5: Comparison Experiment III—Dispersibility and Sieve Testing

Experiments were conducted to determine whether tablets of the invention and tablets of the prior art are dispersible tablets. Tablets manufactured according to Example 1 ("Tablet A"), comprising 25 µg misoprostol, were compared to commercially available Cytotec tablets, comprising misoprostol 0.2 mg.

Dispersibility test were performed using water at room temperature. Two tablets of Tablet A were mixed with 100 ml water (Mixture I), and two tablets of Cytotec were mixed with 100 ml (Mixture II) water in both cases while stirring for 180 seconds. For Tablet A, a dispersion forms within a few seconds. For Cytotec, no dispersion is formed, the tablets disintegrate slowly and a suspension is formed. Upon discontinuing stirring, the dispersion comprising Tablet A remains stable, while precipitate is clearly visible in the bottom of the suspension comprising Cytotec.

The mixtures were poured through sieve screens #20, #30, #40, #60, #80, and #100, having apertures of 900 µm, 600 µm, 400 µm, 250 µm, 200 µm, and 140 µm. For Mixture II it was necessary to continue stirring until just before pouring, in order ensure substantially all of the mixture was poured into the sieve. This was not the case for Mixture I which had formed a stable dispersion.

Figure 1:
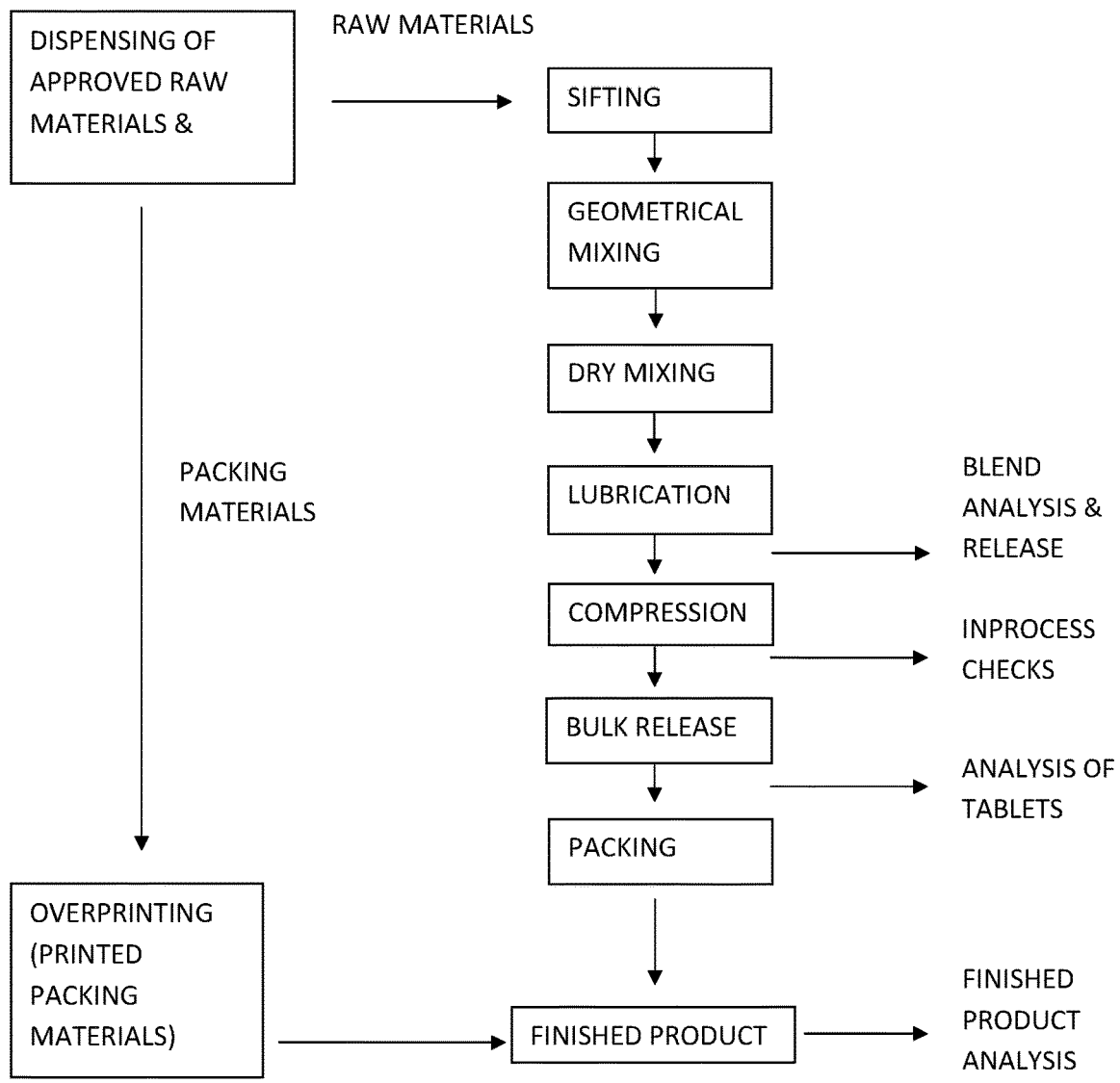
Figure 2A:
FIG. 2A shows the tablets before being subjected to a disintegration experiment. Tablet A is on the left side, Cytotec is on the right side.
Figure 2B:
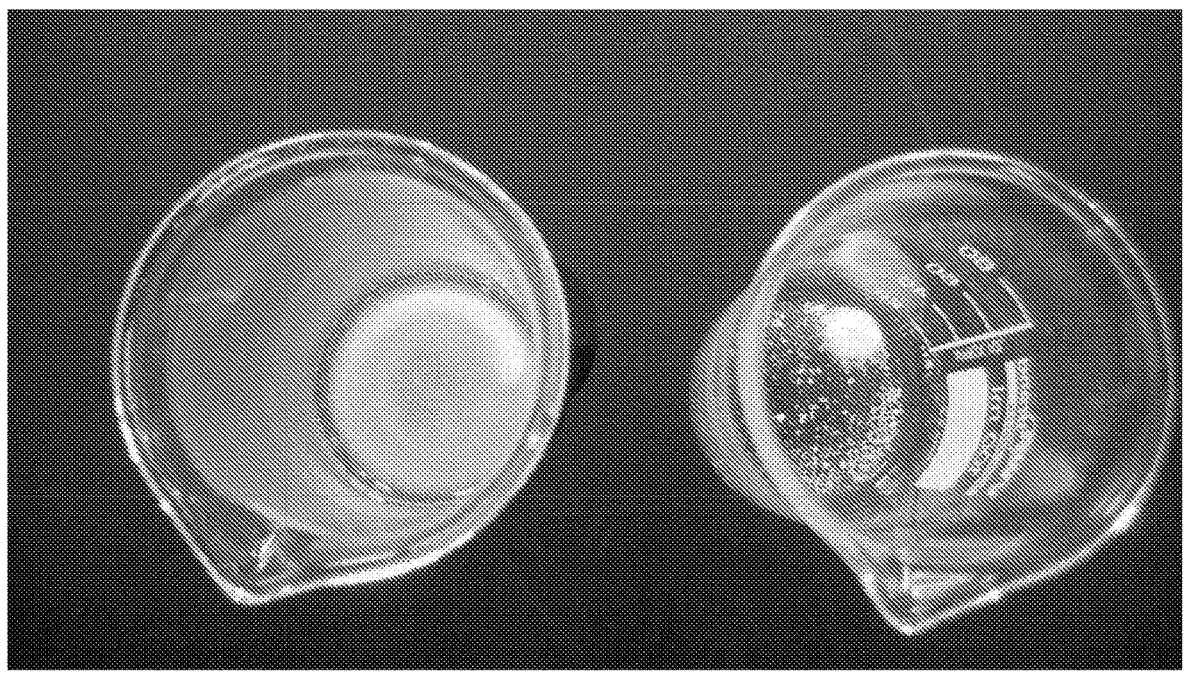
FIG. 2B shows the tablets 3 seconds after being placed in beakers with a few drops of water.
Figure 2C:
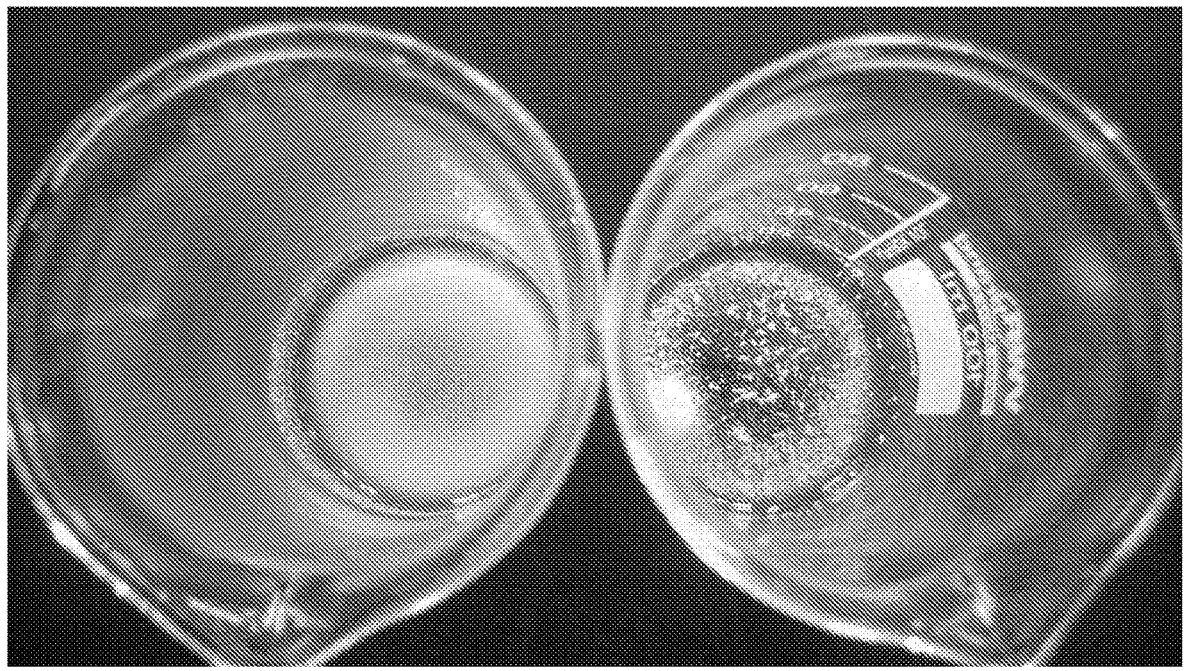
FIG. 2C shows the tablets 7 seconds after being placed in beakers with a few drops of water.
Figure 2D:
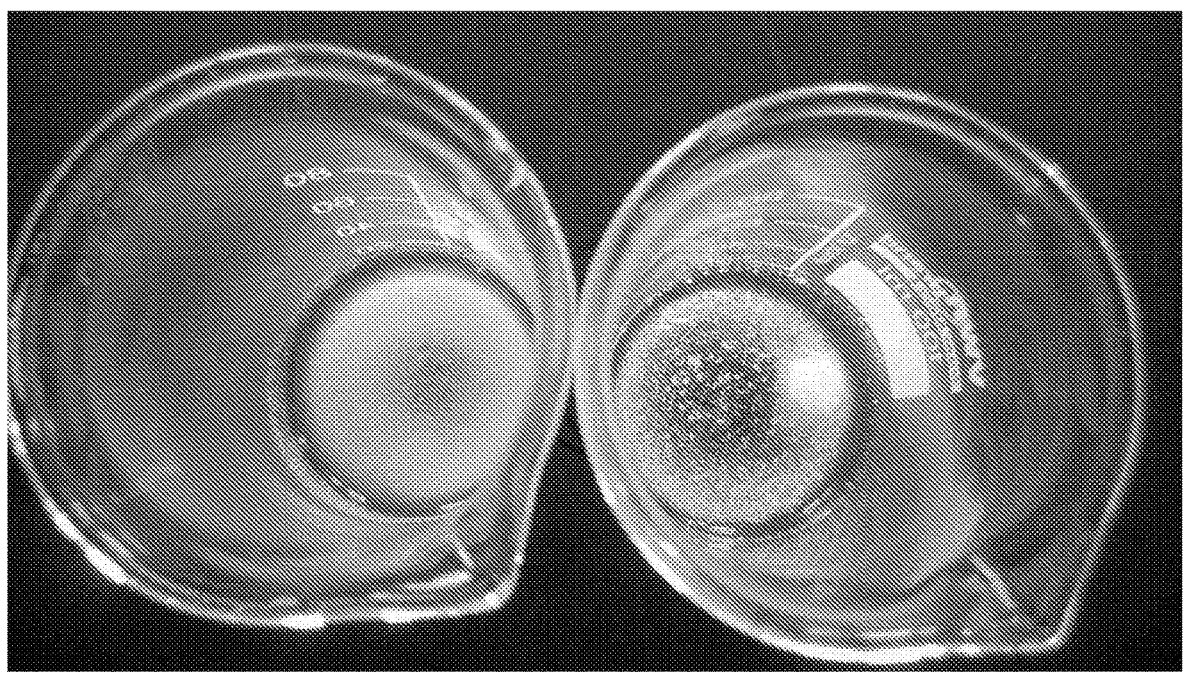
FIG. 2D shows the tablets 15 seconds after being placed in beakers with a few drops of water.
Figure 3A:
Figure 3B:
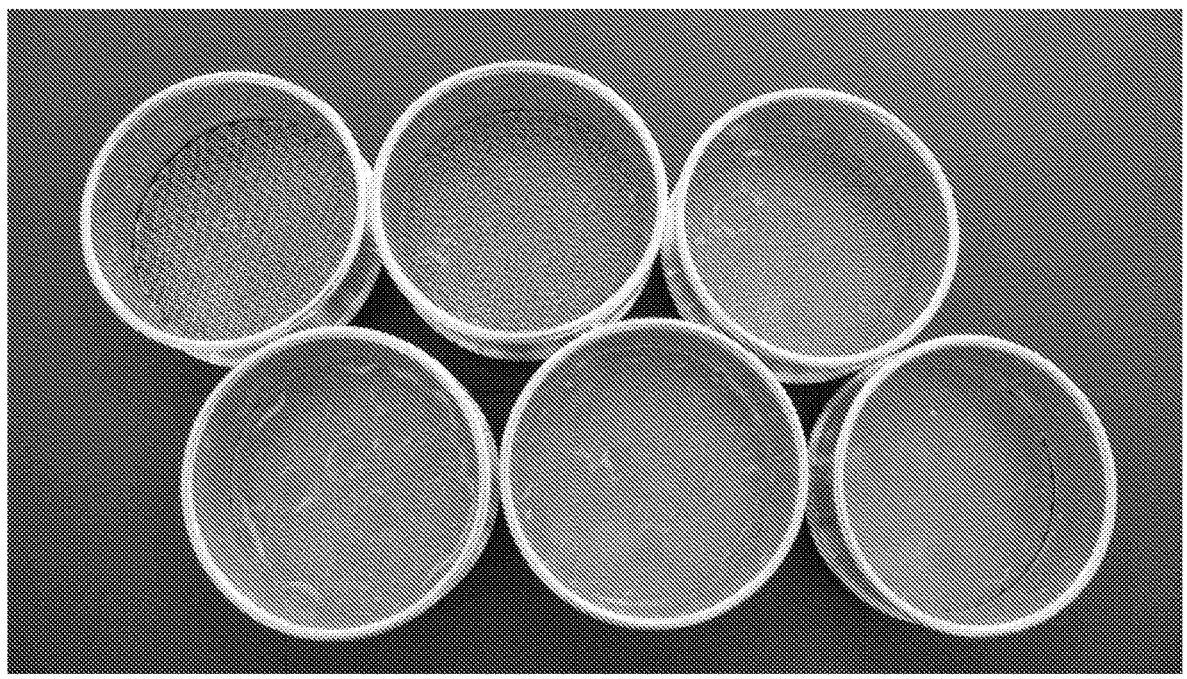

Mixture I, passed through the screens #20, #30, #40 without leaving any trace of precipitate, while a small amount of precipitate was visible in screen #60. At least 90% of the precipitate was apparent in screens #80 and #100 (FIG. 3A upper row, from left to right: sieve #20, #30, #40; lower row: sieve #60, #80, #100). Upon pouring Mixture II through the screens, particles remained in all sieve screens (FIG. 3B upper row, from left to right: sieve #20, #30, #40; lower row: sieve #60, #80, #100).

It was thus confirmed that Tablet A is a dispersible tablet, while Cytotec is not a dispersible tablet.

Additional experiments were conducted using larger amounts of water mixed with the Cytotec tablets, but no dispersions were formed, and particles remained in all the sieve screens.

Example 6: Compositions of the Invention

The table below provides manufactured (A) or contemplated (B and C) compositions of the invention.

|  | Tablet | | |
| --- | --- | --- | --- |
|  | A<br>25 µg tablet<br>(mg/tablet) | B<br>200 µg tablet<br>(mg/tablet) | C<br>200 µg<br>tablet w/o<br>Maize starch<br>(mg/tablet) |
| Misoprostol<br>(as 1% HPMC dispersion) | 2.5 | 20 | 20 |
| Microcrystalline cellulose | 69.5 | 57 | 62 |
| Maize starch | 10 | 5 | 0 |
| Croscarmellose sodium | 10 | 10 | 10 |
| Crospovidone | 10 | 10 | 10 |
| Colloidal anhydrous silica | 1 | 1 | 1 |
| Total (mg) | 103 | 103 | 103 |

Example 7: Clinical Studies

Cytotec tablets contain 200 micrograms (µg) of the active substance, misoprostol. The other ingredients are indicated to be: microcrystalline cellulose, sodium starch glycolate, hydrogenated castor oil, and hypromellose (E464). Cytotec tablets are white to off white hexagonal tablets scored on both sides. According to the package leaflet, the tablets may help prevent getting ulcers in the stomach or duodenum, and can also be used to heal existing ulcers. Patients are warned against using Cytotec if they are pregnant or trying to become pregnant, because it may cause a miscarriage according to the leaflet. According to the leaflet, patients should take two 200 microgram Cytotec tablets twice a day with food, or alternatively one Cytotec tablet four times a day, at regular intervals with food.

Cytotec tablets containing 200 micrograms (µg) misoprostol may be mixed with water to produce mixtures comprising solid residues. Solid tablets according to the invention (Tablet A) comprising 25 µg misoprostol were compared to 200 µg Cytotec tablets mixed with and diluted to 200 ml with water (CYTOTEC), of which either 25 or 50 ml was administered orally. The mixture CYTOTEC is presently used as off-label treatment in Sweden for labor induction. Note that the dosage of 200 µg of the Cytotec tablets make them unsuitable for providing dosages of 25 or 50 µg without division of the tablet. However, the tablets have a hexagonal shape with one groove making it difficult to divide the tablets precisely in ⅛ or ¼ fractions.

A trial was performed giving misoprostol for the induction of labor. The four (4) treatment groups comprise oral administration of 25 µg 2-hourly and 50 µg 4-hourly, comparing Tablet A and CYTOTEC for each administration dosage. Each group consisted of 12 women. The results are provided below. The symbol $t_{1/2}$ denotes the terminal half-life.

| 50 µg 4-hourly | | |
| --- | --- | --- |
| Mean $t_{1/2}$ (hrs) | Tablet A | 0.57 |
|  | CYTOTEC | 0.70 |
| Vaginal delivery | Tablet A | 11 (of 12 women) |
|  | CYTOTEC | 5 (of 12 women) |
| Duration (hrs) of Induction to delivery | Tablet A | 20.5 |
|  | CYTOTEC | 27.5 |
| 25 µg 2-hourly | | |
| Mean $t_{1/2}$ (hrs) | Tablet A | 0.43 |
|  | CYTOTEC | 0.60 |
| Vaginal delivery | Tablet A | 9 (of 12 women) |
|  | CYTOTEC | 11 (of 12 women) |
| Duration (hrs) of Induction to delivery | Tablet A | 17.9 |
|  | CYTOTEC | 25.5 |

These results indicate that the Mean $t_{1/2}$ is shorter for Tablet A than for CYTOTEC. Further, the results indicate that the duration of induction to delivery is shorter for Tablet A than for CYTOTEC. For the 50 µg 4-hourly groups Tablet A provides a desirable higher number of vaginal deliveries (the remaining women being Caesarean or instrumental), than CYTOTEC. For the 25 µg 2-hourly groups, the difference of number of vaginal deliveries appears to be too small to make any conclusion of efficacy upon comparing Tablet A with CYTOTEC.

Without being bound by theory, it may be speculated as follows. Tablet A, which is free from extended release agents because it is designed to be suitable for sublingual administration, provides a shorter $t_{1/2}$ compared to CYTOTEC. The active ingredient is immediately dispersed upon oral administration as a tablet, providing faster uptake of the active ingredient. CYTOTEC has longer $t_{1/2}$ due to the presence of an extended release agent. Apparently, the extended release agent retards the uptake of the active ingredient, even if the Cytotec tablet is administered as a mixture with water. It is speculated that the active ingredient, misoprostol, is intimately mixed with the extended release agent of Cytotec, providing a longer release time, resulting in longer $t_{1/2}$ and leading to longer duration of induction of delivery times. It is speculated that for Tablet A a more sudden increase (followed by decrease) of the concentration of misoprostol, kick-starts processes provoking the shorter duration of induction to delivery times.

The invention claimed is:

1. A method for obtaining cervical ripening or the induction of labor in a subject comprising sublingual or oral administration of a solid pharmaceutical formulation comprising misoprostol or a pharmaceutically acceptable salt thereof, wherein the formulation is administered to the subject as a dosage form that is a tablet having a content of 0.5-50 µg misoprostol, or an equivalent amount of a pharmaceutically acceptable salt thereof, and wherein said dosage form allows dispersion in 100 ml water at 25° C. within 3 minutes upon stirring, thereby providing a dispersion, said dispersion passing through a sieve screen with a nominal mesh aperture of 710 µm, wherein the dosage form cannot pass through the sieve screen before the dispersion in water.

2. The method according to claim 1, wherein the formulation is administered to a pregnant woman.

3. The method according to claim 1, wherein 25-50 µg misoprostol, or an equivalent amount of a pharmaceutically acceptable salt thereof, is administered orally or sublingually every 2-4 hours.

4. The method according to claim 1, providing a duration of induction to delivery of less than 24 hours.

5. The method according to claim 1, wherein said misoprostol or pharmaceutically acceptable salt thereof is the sole active ingredient in said formulation.

6. The method according to claim 1, wherein said pharmaceutical formulation has a content of misoprostol or a pharmaceutically acceptable salt thereof of 0.005%-2% by weight of the pharmaceutical formulation.

7. The method according to claim 1, wherein said pharmaceutical formulation has a content of misoprostol or a pharmaceutically acceptable salt thereof of less than 2% by weight of the pharmaceutical formulation.

8. The method according to claim 1, wherein said dosage form is a tablet having a score line.

9. The method according to claim 8, wherein said score line allows fractional dosing.

10. The method according to claim 8, wherein said score line allows fractional dosing of ½ or ¼ of the total dosage of said pharmaceutical formulation.

11. The method according to claim 1, wherein said dosage form has a disintegration time of less than 3 minutes as measured using Disintegration Apparatus A according to European Pharmacopoeia 8.0, said Disintegration Apparatus A having a basket containing six tubes, placing one tablet in each of the six tubes without a disc, and operating the apparatus using water as the immersion fluid, maintained at 37±2° C.

12. The method according to claim 11, wherein said dosage form has a disintegration time of less than 2 minutes.

13. The method according to claim 11, wherein said dosage form has a disintegration time of less than 1 minute.

14. The method according to claim 11, wherein said dosage form has a disintegration time of less than 45 seconds.

15. The method according to claim 11, wherein said dosage form has a disintegration time of less than 30 seconds.

16. The method according to claim 1, wherein said dosage form allows dispersion in 100 ml water at 25° C. within 2 minutes upon stirring, thereby providing a dispersion, said dispersion passing through a sieve screen with a nominal mesh aperture of 710 μm.

17. The method according to claim 1, wherein said dosage form allows dispersion in 100 ml water at 25° C. within 1 minute upon stirring, thereby providing a dispersion, said dispersion passing through a sieve screen with a nominal mesh aperture of 710 μm.

18. The method according to claim 1, wherein said dosage form allows dispersion in 100 ml water at 25° C. within 5 minutes, substantially without stirring, thereby providing a dispersion, said dispersion passing through a sieve screen with a nominal mesh aperture of 710 μm.

19. The method according to claim 1, wherein said dosage form is in form of a dispersible tablet, which is dispersed in water before administration, providing a homogeneous dispersion; wherein said dispersible tablet disintegrates within 3 minutes using water at 15-25° C. forming a dispersion; wherein the fineness of said dispersion complies with a test comprising placing 2 of said dispersible tablets in 100 ml water and stirring until completely dispersed, whereby a smooth dispersion is produced, which passes through a sieve screen with a nominal mesh aperture of 710 μm.

20. The method according to claim 1, wherein said dosage form is in form of a dispersible tablet, which is dispersed in water before administration, providing a homogeneous dispersion; wherein said dispersible tablet disintegrates within 3 minutes using water at 20° C. forming a dispersion; wherein the fineness of said dispersion complies with a test comprising placing 2 of said dispersible tablets in 100 ml water and stirring until completely dispersed, whereby a smooth dispersion is produced, which passes through a sieve screen with a nominal mesh aperture of 400 μm.

21. The method according to claim 1, wherein said dosage form is in form of an immediate release tablet.

22. The method according to claim 1, wherein said pharmaceutical formulation is free of any extended release agents.

23. The method according to claim 1, wherein said dosage form comprises a coating.

24. The method according to claim 1, wherein said pharmaceutical formulation comprises misoprostol or a pharmaceutically acceptable salt thereof as the sole active ingredient and a superdisintegrant; and wherein said superdisintegrant is present in an amount of 6-50% by weight, and wherein said superdisintegrant is selected from the group consisting of modified starches, modified celluloses, cross-linked polyvinylpyrrolidone, soy polysaccharide, cross-linked alginic acid or sodium or potassium salts thereof, gellan gum, xanthan gum, calcium silicate, ion exchange resins, *Cassia fistula* gum, *Lepidum sativum* , locust bean gum, *Plantago ovate* mucilage, seed powder, *Plantago ovata* husk powder, treated agar, and synthetic superdisintegrants.

* * * * *